United States Patent
Ma et al.

(10) Patent No.: US 7,662,614 B2
(45) Date of Patent: Feb. 16, 2010

(54) BIOCHIP PLATFORM INCLUDING DIELECTRIC PARTICLE LAYER AND OPTICAL ASSAY APPARATUS USING THE SAME

(75) Inventors: Jang-seok Ma, Seongnam-si (KR); Heon-su Jeon, Gunpo-si (KR); Soo-hyung Choi, Hwaseong-si (KR); In-ho Lee, Yongin-si (KR); Fu Wang, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 78 days.

(21) Appl. No.: 11/330,566

(22) Filed: Jan. 11, 2006

(65) Prior Publication Data

US 2006/0189002 A1    Aug. 24, 2006

(30) Foreign Application Priority Data

Jan. 14, 2005  (KR)  ............... 10-2005-0003796
Nov. 1, 2005   (KR)  ............... 10-2005-0103789

(51) Int. Cl.
    *C12M 1/34*   (2006.01)
(52) U.S. Cl. ............... 435/288.7; 435/287.1; 435/287.9
(58) Field of Classification Search ............ 435/6, 435/4, 7.92, 283.1, 287.1–287.3, 287.9, 7.1; 422/55; 356/244, 246
    See application file for complete search history.

(56) References Cited

U.S. PATENT DOCUMENTS

| | | | | |
|---|---|---|---|---|
| 5,677,196 A | * | 10/1997 | Herron et al. | ............... 436/518 |
| 5,705,813 A | * | 1/1998 | Apffel et al. | ............... 250/288 |
| 6,294,392 B1 | * | 9/2001 | Kuhr et al. | ............... 436/518 |
| 6,437,345 B1 | | 8/2002 | Bruno-Raimondi et al. | ...... 250/458.1 |
| 6,454,924 B2 | | 9/2002 | Jedrzejewski et al. | ....... 204/601 |
| 6,572,830 B1 | * | 6/2003 | Burdon et al. | ......... 422/186.29 |
| 6,752,868 B2 | * | 6/2004 | Lewis et al. | ................... 117/68 |
| 6,800,709 B2 | * | 10/2004 | Aert et al. | ................... 526/229 |
| 7,105,352 B2 | * | 9/2006 | Asher et al. | ................... 436/94 |
| 7,343,074 B1 | * | 3/2008 | Gallagher et al. | ........... 385/125 |
| 2002/0118435 A1 | * | 8/2002 | Foulger et al. | .............. 359/265 |
| 2002/0167984 A1 | | 11/2002 | Scherer | |
| 2003/0012693 A1 | | 1/2003 | Otillar et al. | |

* cited by examiner

*Primary Examiner*—Ann Y Lam
(74) *Attorney, Agent, or Firm*—Cantor Colburn LLP

(57) ABSTRACT

Provided are a biochip platform for biochemically analyzing a sample such as DNA or protein, including a dielectric particle layer, and an optical assay apparatus including the same. The biochip platform includes the dielectric particle layer uniformly formed on a substrate. The particle uniformity of the dielectric particle layer enables good wavelength separation of fluorescence signal, and the large surface area of the dielectric particle layer guarantees better amplifications efficiency of fluorescence signal. Furthermore, the biochip platform shows good economical efficiency due to easy fabrication process, and is particularly useful in an optical assay apparatus for analyzing a biochemical sample due to good assay efficiency.

29 Claims, 11 Drawing Sheets

BIOCHIP PLATFORM INCLUDING DIELECTRIC PARTICLE LAYER AND OPTICAL ASSAY APPARATUS USING THE SAME

CROSS-REFERENCE TO RELATED PATENT APPLICATION

This application claims priority from Korean Patent Application No. 10-2005-0003796, filed on Jan. 14, 2005, and 10-2005-0103789, filed on Nov. 1, 2005, in the Korean Intellectual Property Office, the disclosure of which is incorporated herein in its entirety by reference.

1. Field of the Invention

The present invention relates to a biochip platform for biochemically analyzing a sample, and more particularly, to a biochip platform for biochemically analyzing a sample such as DNA or protein, including a dielectric particle layer, and an optical assay apparatus including the biochip platform.

2. Description of the Related Art

In biochemical sample assays, various assay methods using two-dimensional arrays, such as Enzyme-Linked ImmunoSorbent Assay (ELISA), are known. Among these assay methods, fluorescence assay methods have been widely used.

Generally, a fluorescence assay apparatus includes a fluorescent marker-labeled sample, and a light source, such as laser, for inducing fluorescence emission from the sample. When excitation light is irradiated onto the sample, fluorescence is emitted from a fluorescent material in the sample. The fluorescence from the fluorescent material is monitored by an optical detector. At this time, generally, an optical fiber waveguide is used to guide light reflected from the sample to a sensor. However, the optical fiber waveguide totally depends on internal reflection, and thus, incident light is confined and guided in the fiber core.

For this reason, in conventional fluorescence assay techniques, a considerable amount of fluorescence light is not focused on an optical detector, thereby leading to fluorescence loss. Such fluorescence loss results in an inevitable increase in detection limit, and a decrease in sensitivity in a high-sensitivity test. Furthermore, in many cases, much signal loss is caused due to low signal-to-noise level.

Meanwhile, an evanescent wave sensing technique is also known. This technique utilizes laser light which is trapped in a very thin layer and creates an evanescent field which extends a short distance from a physical sensor. The evanescent field can interact with molecules attached to the surface of the sensor. This evanescent excitation or interaction occurs at only a region very close to a waveguide. The evanescent field is spatially localized, and energy stored in the evanescent field is not transferred to other regions.

In order to solve the problems of the above-described fluorescence assay methods, many efforts have been made to develop a fluorescence assay technique which offers a high signal-to-noise level, utilizes a less number of optical devices, and simplifies fabrication process and fluorescence measurement.

U.S. Pat. No. 6,437,345, issued to Zeptosens, discloses a detection device using diffraction gratings and evanescent field. According to the patent document, only a surface reactive material (i.e., within the depth of several hundreds nm from the surface) can be selectively excited, thereby leading to a relatively high signal-to-noise level. However, a submicron pattern fabrication process is very complicated, and a precise mechanical structure is needed for light trapping using diffraction gratings. In addition, the use of diffraction gratings and evanescent field reduces the luminous efficiency of a light source, and thus, it is necessary to use a detection device with high sensitivity.

Infineon (Germany) has developed a porous silicon-based biochip using chemiluminescence. The porous silicon has a large surface area, and thus, it is possible to increase the concentration of reactants. Further, no light source is need for chemiluminescence, and thus, fluorescence interference does not occur, thereby increasing a signal-to-noise level. However, it is very difficult to fabricate micron-scale porous silicon, chemiluminescence involves a complex reaction process and a cost increase, and a detection device with high sensitivity is needed.

U.S. Pat. No. 6,454,924, issued to Zyomyx, discloses a fluorescence assay method using a micropole. According to the method, a contrast can be increased, but the fabrication process for the micropole is complicated, and a special device for surface reaction in a patterned pole and a detection device with high sensitivity are needed.

Thus, the present invention is directed to develop a high sensitivity fluorescence assay apparatus that can overcome the above-described problems of conventional fluorescence assay apparatuses, is easy in fabrication and fluorescence measurement, and is cost-effective.

SUMMARY OF THE INVENTION

The present invention provides a biochip platform which can efficiently separate and amplify a fluorescence signal, and is easy in fabrication and fluorescence measurement.

The present invention also provides a fluorescence assay apparatus including the biochip platform.

According to an aspect of the present invention, there is provided a biochip platform including: a substrate; and a dielectric particle layer formed on the substrate.

The dielectric particle layer may have a photonic crystal structure.

The photonic crystal structure may be a face-centered-cubic (FCC) structure.

Probes may be attached to surfaces of dielectric particles constituting the dielectric particle layer.

A labeling material contained in a target material binding with the probes may generate light ranging from 300 nm (UV-VIS) to 1,500 nm (near IR) by a light source.

The light generated from the labeling material may correspond to an energy bandgap of the photonic crystal structure.

The energy bandgap of the phhotonic crystal structure may be determined by the particle size of the dielectric particles or refractive index.

The probes may be attached to the surfaces of the dielectric particles via a surface-treatment agent.

The probes may be oligonucleotides or proteins.

The dielectric particles of the dielectric particle layer may be made of a dielectric material selected from silica, ZnSe, CdS, polystyrene, polymethylmethacrylate (PMMA), and $Fe_3O_4$.

The dielectric particles of the dielectric particle layer may have an average particle size of 100 to 1,000 nm and may be spherical.

The dielectric particle layer may have a thickness of 100 nm to 100 μm.

The dielectric particle layer may be formed by gravity sedimentation or evaporation.

The substrate may be a transparent substrate.

The transparent substrate may be a glass substrate coated with $TiO_2$, $SiN_3$, or indium tin oxide (ITO), or a Si substrate.

According to another aspect of the present invention, there is provided an optical assay apparatus including: a light source generating excitation light for exciting a sample; the above-described biochip platform; and a detector detecting detection light from the sample.

The excitation light from the light source may be incident into the dielectric particle layer of the biochip platform or a bottom surface of the substrate.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1A:
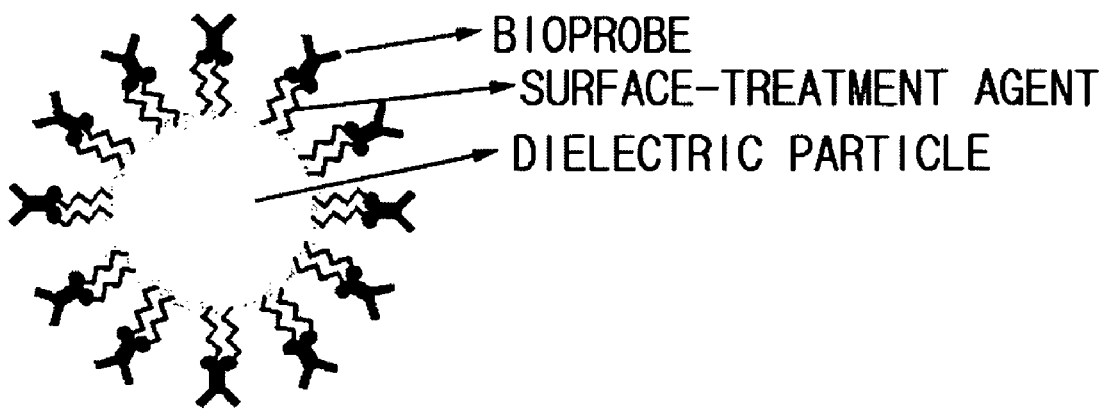
FIG. 1A is a schematic diagram illustrating a dielectric particle including a surface-treatment agent and bioprobes according to the present invention.

The present invention will now be described more fully with reference to the accompanying drawings, in which exemplary embodiments of the invention are shown.

The present invention provides a biochip platform including a substrate, and a spherical dielectric particle layer disposed on the substrate.

In view of low detection sensitivity of conventional platforms, the biochip platform of the present invention is directed to enhance detection sensitivity. That is, in the biochip platform of the present invention, a spherical dielectric particle layer is formed on a transparent substrate, and a target sample is attached to a surface of the dielectric particle layer to thereby measure fluorescence. The particle uniformity of the dielectric particle layer enables good wavelength separation of fluorescence signal, and the large surface area of the dielectric particle layer guarantees better amplification efficiency of fluorescence signal.

Meanwhile, a fluorescence signal from a sample may be absorbed into or scattered from the dielectric particle layer, thereby causing fluorescence signal loss. To solve this problem, the dielectric particle layer may have a photonic crystal structure. In particular, a $SiO_2$ photonic crystal structure has a function capable of transmitting and/or reflecting a predetermined wavelength light, and thus, can transmit and/or reflect a fluorescence signal from a sample without absorbing the fluorescence signal, thereby minimizing fluorescence signal loss. That is, a photonic crystal structure has an energy bandgap in a predetermined wavelength region. When a fluorescence signal from a sample corresponds to the energy bandgap, internal reflection efficiency is increased, thereby decreasing the amplification efficiency of the fluorescence signal.

There are various types of a photonic crystal structure. For example, the photonic crystal structure may be a face-centered-cubic (FCC) structure, a diamond-like structure, an inverse opal structure, etc. The FCC structure is geometrically preferable due to the highest packing density (0.740) and a high surface volume ratio (2.22/r, r is sphere radius).

Bioprobes for binding with a target material are present on surfaces of spherical dielectric particles of the dielectric particle layer having the above-described photonic crystal structure. These bioprobes are attached to surfaces of the spherical dielectric particles, and then bind with a target material in a sample to generate fluorescence. At this time, the fluorescence is induced from a labeling material attached to the target material, and may have a wavelength range of 300 to 1,500 nm so that fluorescence detection is achieved in a visible light wavelength range. In particular, as described above, when the fluorescence corresponds to the energy bandgap of the dielectric particle layer having the photonic crystal structure, internal reflection efficiency is increased, thereby decreasing signal amplification efficiency. The energy bandgap of the photonic crystal structure is determined by the particle size of the dielectric particles forming the photonic crystal structure or an effective refractive index. As the particle size or the effective refractive index increases, longer wavelength light is specifically reflected.

The bioprobes attached to surfaces of the dielectric particles of the dielectric particle layer may be oligonucleotides or proteins, and more preferably, DNAs, RNAs, PNAs, aptamers, antibodies, antigens, or haptens.

Figure 1B:
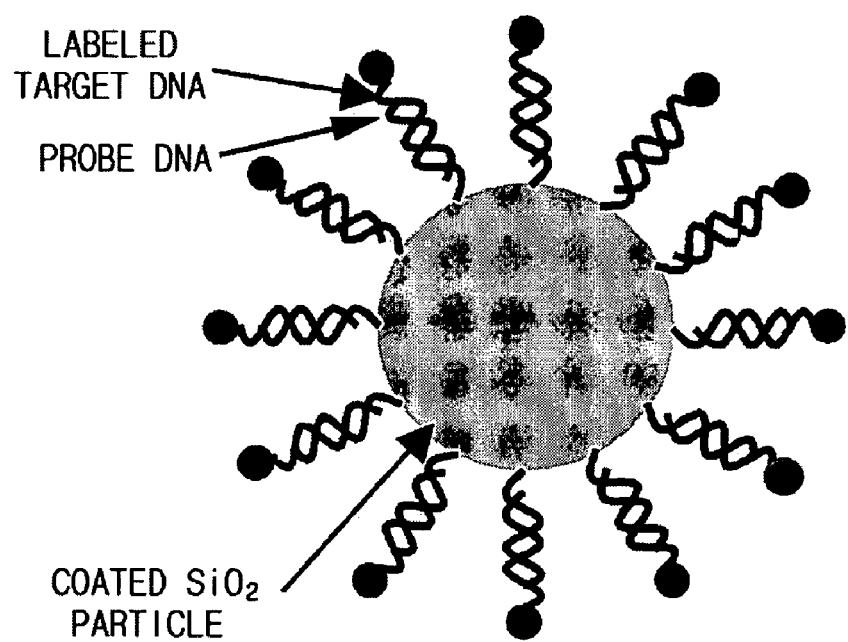
FIG. 1B is a schematic diagram illustrating DNA hybridization according to the present invention.

The bioprobes may be directly attached to surfaces of the dielectric particles. However, in view of attachment efficiency, it is preferable that the dielectric particles are treated with a surface-treatment agent, and the bioprobes are attached to the dielectric particles via the surface-treatment agent as a linker (see FIG. 1A). The surface-treatment agent may be silanes, epoxies, carboxyls, amines, aldehydes, etc. More specifically, the surface-treatment agent may be aminopropyltriethoxysilane (APTES), glycidoxypropyltrimethoxysilane (GPTS), triethoxysilane undecanoic acid (TETU), poly(lysine), 4-trimethoxysilylbenzaldehyde, etc. In particular, referring to FIG. 1B, probe DNAs are attached to a surface of a surface-modified particle, and target DNAs are specifically bound to the probe DNAs by DNA hybridization. The DNA hybridization is detected by fluorescence emitted from a labeling material attached to the target DNAs.

The dielectric particles constituting the dielectric particle layer must be periodically arranged and permit the bioprobes to be easily attached to their own surfaces; Thus, the dielectric particles may be made of silica, ZnSe, CdS, polystyrene, polymethylmethacrylate (PMMA), $Fe_3O_4$, etc. The dielectric particles may be made of a dielectric material having a dielectric constant of 1 to 16, and may have spherical shapes. In particular, the dielectric particles may have an average particle size of 100 to 1,000 nm. If the average particle size of the dielectric particles exceeds 1,000 nm, the area of surfaces of the dielectric particles to which the bioprobes can be attached may be insufficient, and it may be difficult to form colloidal particles. On the other hand, if it is less than 100 nm, a pore size may be excessively decreased due to too small particle size, thereby causing the capturing of an unwanted material in pores, resulting in a reduction in fluorescence signal.

The spherical dielectric particles are stacked on a substrate to form a three-dimensional stack structure (or photonic crystal structure). The thickness of the stack structure may be 100 nm to 100 µm. If the thickness of the stack structure is less than 100 nm, a sufficient amount of samples may not be attached due to low surface area, which makes it difficult to separate and amplify a fluorescence signal. On the other hand, if it exceeds 100 µm, excitation light from a light source may not sufficiently reach the surfaces of the particles inside the particle layer, which makes it difficult to achieve sufficient amplification efficiency.

When the dielectric particle layer is composed of spherical colloidal particles, the spherical colloidal particles can form a FCC structure. The FCC structure is a thermodynamically stable, dense structure that the particles are uniformly and periodically arranged. Also, the FCC structure is a structure that sufficient pores are present between adjacent ones of the particles and thus the bioprobes can be attached to the particles through the pores. Such pores enable fluid flow through channels of a size of 5 mm to 500 nm connecting the pores, thereby ensuring the attachment of the bioprobes to surfaces of more particles.

The substrate on which the dielectric particle layer is formed is not particularly limited and may be any substrate known in the art. However, when excitation light from a light source is incident into a bottom surface of the substrate, a transparent substrate can be used so that the excitation light from the light source is easily incident into the bottom surface of the substrate. Thus, the substrate may be a glass coated with $TiO_2$, $SiN_3$, or indium tin oxide (ITO), or a Si substrate.

The formation of the dielectric particle layer on the substrate may be performed using various methods known in the art, e.g., gravity sedimentation, solvent evaporation, capillary force, or spin coating.

Figure 2A:
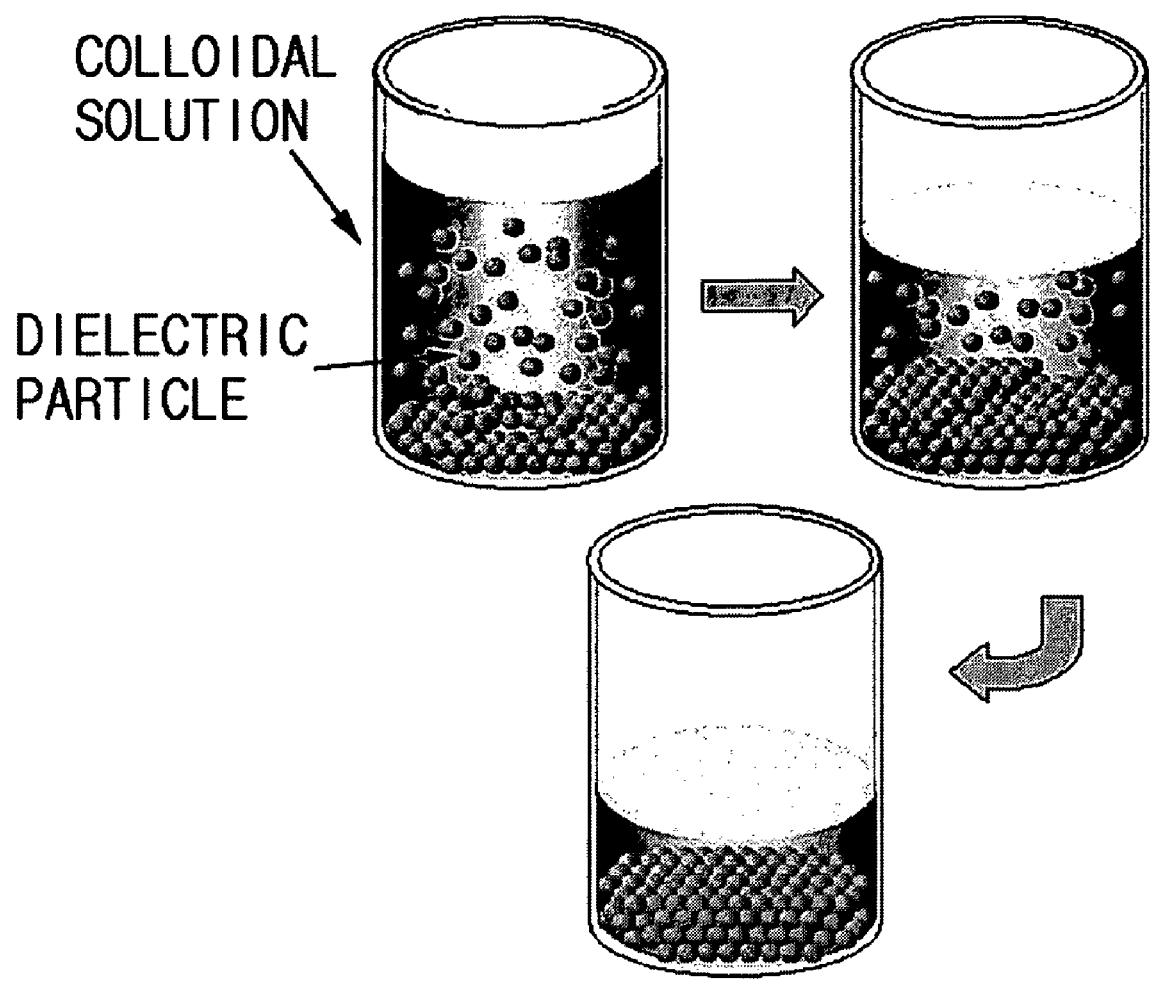
FIG. 2A is a view illustrating a process of forming a dielectric particle layer using gravity sedimentation according to the present invention.

In gravity sedimentation, as shown in FIG. 2A, a colloid solution containing particles is left for a long time so that the particles are settled by gravity. According to this method, a particle layer with a periodic particle array can be easily and spontaneously formed on a substrate. A capillary force method is carried out on a vertically-disposed substrate using capillary force, and formation of a particle layer using spin coating is carried out by adjusting a spin rate. Among the above methods, the gravity sedimentation has a difficulty in controlling the thickness of a particle layer, but guarantees easy formation of the particle layer as described above. A dielectric particle layer formed by gravity sedimentation may have a poor surface smoothness. Thus, excitation light from a light source may be incident into a bottom surface of a substrate. In this case, as described above, a transparent substrate may be used. On the contrary, the capillary force method and the spin coating method have a difficulty in forming a particle layer, but can easily control the thickness of the particle layer.

In more detail, with respect to the capillary force method, dielectric particles with a predetermined particle size are dispersed in distilled water or alcohol. Then, a substrate is dipped in the resultant colloidal sol and dried. With respect to the spin coating method, a substrate is etched with hydrofluoric acid using a photoresist pattern followed by photoresist removal to define projections and recesses. When a colloidal sol is dropped onto the substrate while rotating the substrate, dielectric particles are packed in the recesses of the substrate.

With respect to the gravity sedimentation, a colloid solution containing dielectric particles is applied onto a substrate in a vessel and left for a long time so that the particles form a particle layer on the substrate by downward force of gravity. In more detail, when colloidal dielectric particles with a particle size of 400 to 700 nm are left in a minimal external vibration condition, they are gradually settled downward and stacked from a top surface of a substrate by gravity and thermal agitation. In this case, commercially available dielectric particles may be used. Alternatively, relatively uniform spherical particles prepared by a Stober process may also be used. The dielectric particles can form a FCC or HCP (hexagonal close-packed) structure with in-plane triangular ordering of the particles. However, a thermodynamically stable FCC structure is generally used. When a solvent present in pores defined between the spherical dielectric particles is gradually evaporated, a so-called "opal" structure is formed. To incorporate other material into the pores between the dielectric particles, the opal structure may be sintered at high temperature so that necks are formed between the dielectric particles.

Figure 2B:
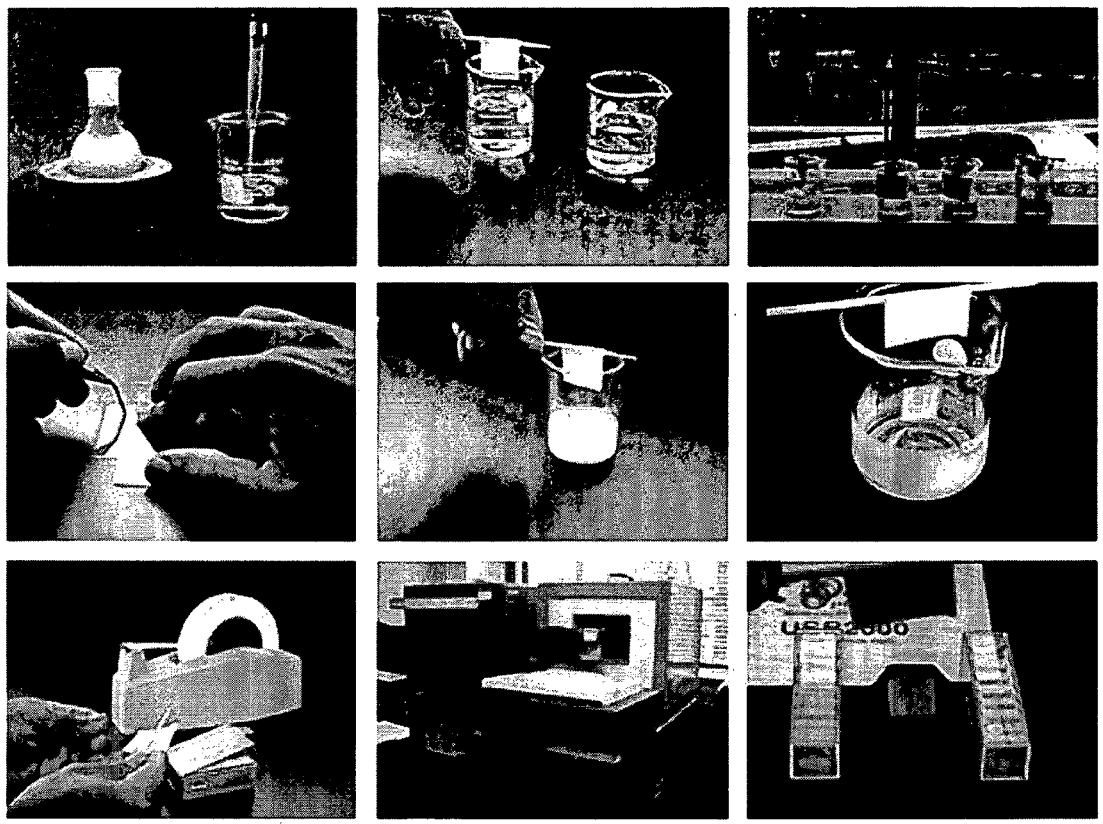
FIG. 2B is an conventional image showing a process of forming a dielectric particle layer using evaporation (vertical dip coating)

Solvent evaporation is a simple method for formation of a dielectric particle layer and film thickness control. Referring to FIG. 2B showing solvent evaporation, dielectric particles are mixed with a solvent by suspension, dispersion, colloidal dispersion, or dissolution, and a substrate is dipped thereto. With solvent evaporation, the dielectric particles are accumulated on the substrate to thereby form a dielectric particle layer. The thickness of the dielectric particle layer can be appropriately controlled by appropriately selecting a solvent and evaporation conditions. The reason why the thickness control of a dielectric particle layer is important is because reflection wavelength can be affected by the thickness of the dielectric particle layer according to Equation given as reflection wavelength=2×refractive index×thickness, thereby affecting amplification efficiency.

A solvent that can be used in solvent evaporation may be selected from strong volatile organic solvents known in the art, e.g., alcohols or benzenes, but is not particularly limited. However, it is preferable that solvent evaporation conditions including temperature and pressure are optimally determined considering the utilization of a biochip platform since the array shape of dielectric particles may be affected by the solvent evaporation conditions. The solvent may be evaporated in atmospheric pressure or in a vacuum state at a temperature of 10 to 40° C.

As described above, after the dielectric particle layer is formed on the substrate, the resultant structure may be sintered in an appropriate temperature range to ensure a more stable binding between the dielectric particle layer and the substrate. By doing so, the dielectric particle layer can form a stable photonic crystal structure due to a stronger binding between the particles and the substrate. The sintering may be performed at a temperature of 400 to 800° C. for 1 to 10 hours, but the present invention is not limited to the above-illustrated example. The sintering conditions can be easily determined according to a solvent used, the thickness of a particle layer, etc. by those of ordinary skilled in the art.

When the optional sintering process is terminated, the dielectric particles are coated with a surface-treatment agent. The coating with the surface-treatment agent may also be optionally performed. In particular, the coating with the surface-treatment agent is determined by the type of bioprobes. That is, when using bioprobes capable of being easily bound to surfaces of the dielectric particles, the coating with the surface-treatment agent may be omitted. However, when using bioprobes having difficulties in binding with surfaces of the dielectric particles, the surface-treatment agent can be formed as a linker on surfaces of the dielectric particles, thereby facilitating a binding between the probes and the dielectric particles, resulting in fluorescence signal amplification.

The surface-treatment agent coated on surfaces of the dielectric particles is not limited provided that it is a material capable of being bound to surfaces of the dielectric particles and having a functional group capable of binding with the bioprobes. At this time, the binding between the dielectric particles and the surface-treatment agent can be achieved by a physical or chemical bond. All common linker materials that can form a self-assembly with the dielectric materials can be used as the surface-treatment agent. For example, the surface-treatment agent may be silanes, epoxies, carboxyls, amines, or aldehydes. Exemplary examples thereof are as described above.

The bioprobes are attached to the dielectric particles formed on the substrate. As described above, the bioprobes may be oligonucleotides or proteins. The attachment of the bioprobes to the dielectric particles may be performed using a method known in the art, e.g., self-assembled monolayer coating, dip coating, spin coating, LB coating, or printing. After the bioprobes are attached to the dielectric particles, a target material specifically reacting with the bioprobes is added as a sample. The target material is an analyte of interest specifically reacting with the bioprobes, and may include an excitation component which is excited by excitation light, i.e., a labeling material. The excitation component may be a fluorescent material.

The present invention also provides an optical assay apparatus including the above-described biochip platform. The optical assay apparatus includes a light source generating excitation light for exciting a sample, the above-described biochip platform, and a detector detecting a detection beam from the sample. The optical assay apparatus may further include an optical waveguide, a lens, etc.

Figure 6A:
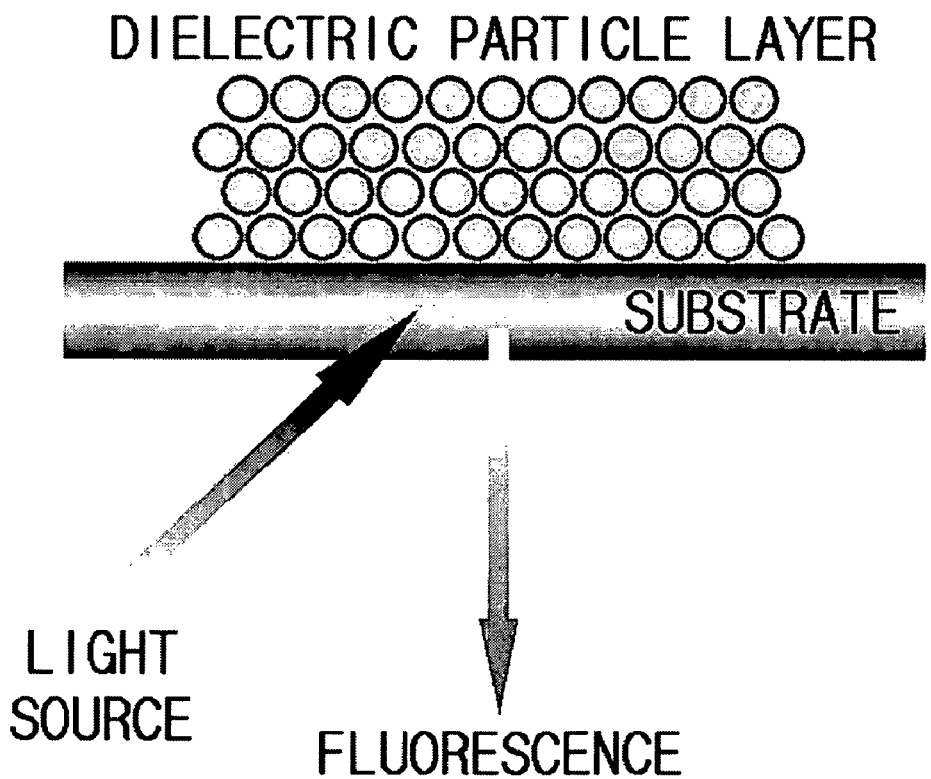
FIG. 6A is a schematic diagram illustrating a fluorescence assay method using a chip platform according to the present invention and a light source irradiating excitation light onto a bottom surface of a substrate of the chip platform.
Figure 6B:
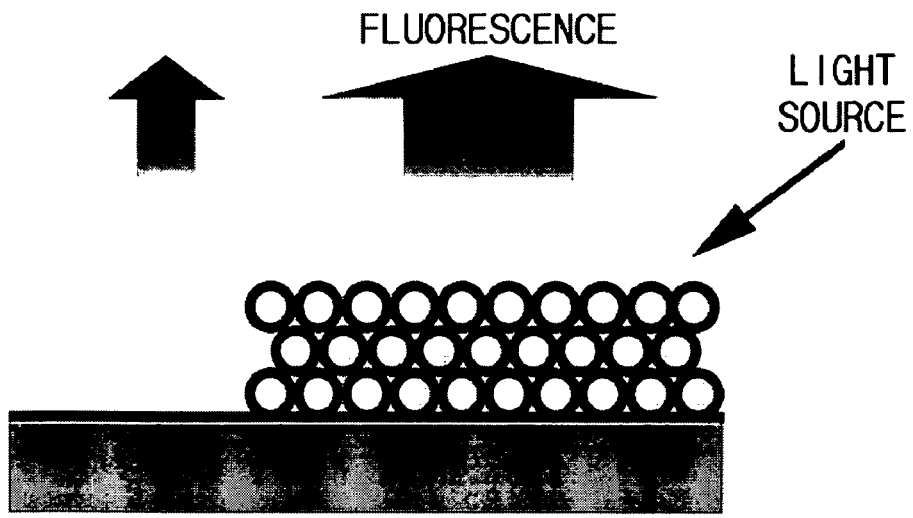
FIG. 6B is a schematic diagram illustrating a fluorescence assay method using a chip platform according to the present invention and a light source irradiating excitation light into a top surface of a substrate of the chip platform.

The optical assay apparatus irradiates excitation light onto the biochip platform, and detects a detection beam, such as fluorescence, emitted from the biochip platform. The excitation light may be incident into a top surface of a substrate on which a dielectric layer is formed, as shown in FIG. 6B. However, in a case where the top surface of a substrate is uneven, and thus a detection beam does not have a homogeneous property such as uniform direction and intensity, the excitation light may also be incident into a bottom surface of the substrate opposite to a dielectric particle layer, as shown in FIG. 6A. For the latter case, the excitation light is incident into a particle layer uniformly formed on the bottom surface of the substrate, and then excites samples. Therefore, a detection beam with more uniform intensity and shape can be generated.

Hereinafter, the present invention will be described more specifically with reference to the following examples. The following examples are for illustrative purposes and are not intended to limit the scope of the invention.

EXAMPLE 1

Figure 3:
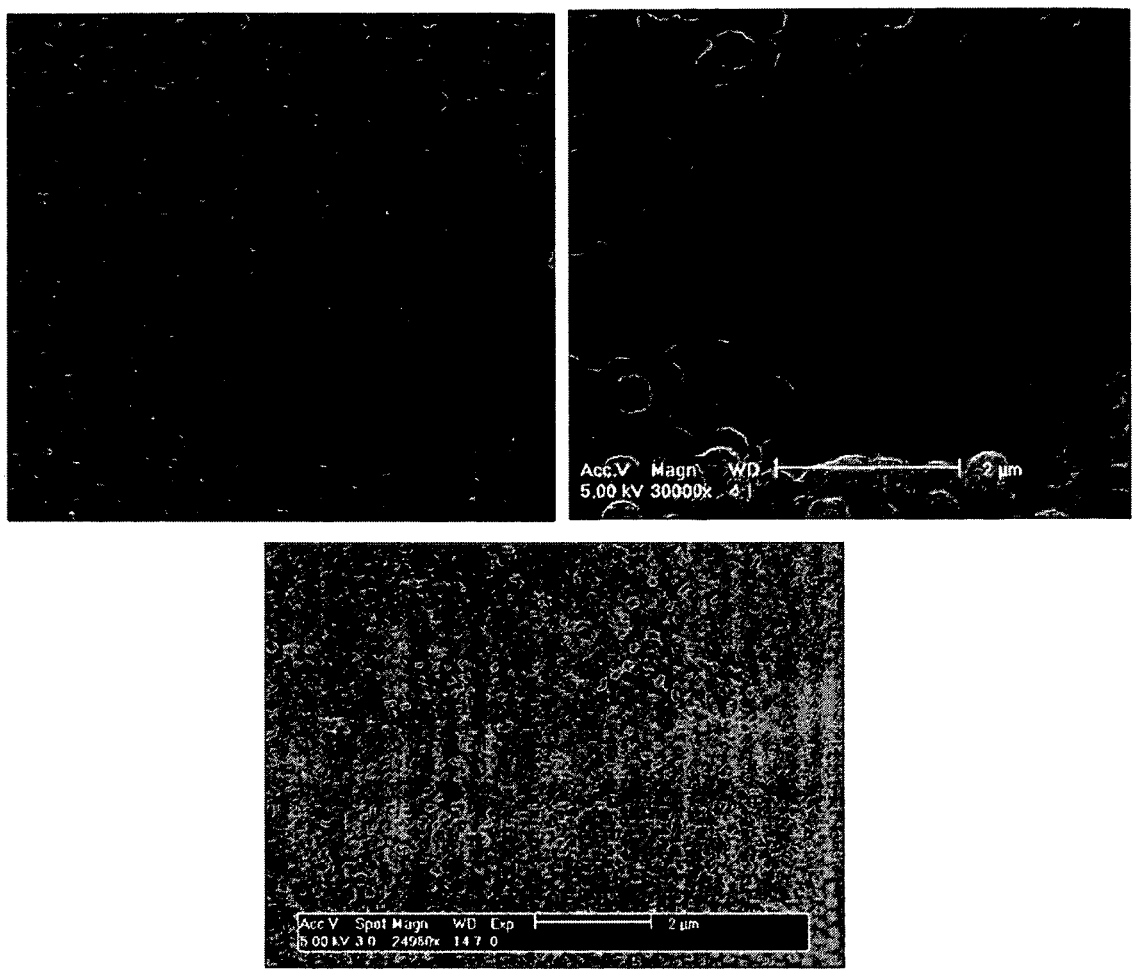
FIG. 3 is a Scanning Electron Microscopic (SEM) image showing a dielectric particle layer with an average particle size of about 575 nm according to the present invention.

Silica ($SiO_2$) particles with a particle size of about 200 to 300 nm were dispersed in water to prepare a colloid solution. The colloid solution was applied to a vessel containing a glass substrate with a size of 1 inch×3 inch and left for 48 hours so that the silica particles were gradually settled by gravity and thermal agitation to thereby form a silica particle layer having a FCC structure and an average thickness of 10 μm on the glass substrate. Then, GAPS (3-aminopropyltrimethoxysilane) used as a surface-treatment agent was self-assembled onto the particle layer to thereby manufacture a biochip platform. An image of the silica particle layer is shown in FIG. 3.

EXAMPLE 2

Silica ($SiO_2$) particles with a particle size of about 200 to 300 nm were dispersed in water to prepare a colloid solution. The colloid solution was applied to a vessel containing a glass substrate with a size of 1 inch×3 inch and left for 48 hours so that the silica particles were gradually settled by gravity and thermal agitation to thereby manufacture a biochip platform in which a silica particle layer having a FCC structure and an average thickness of 10 μm was formed on the glass substrate.

EXAMPLES 3-4

GAPS was coated on surfaces of the silica particles of silica particle layers obtained in the same manner as in Examples 1-2 using dip coating. Then, Alexa Fluor 532-labeled human IG antibody specifically reacting GAPS was attached to surfaces of the silica particles by its covalent bond with GAPS using a wetting method.

EXAMPLE 5

Figure 4A:
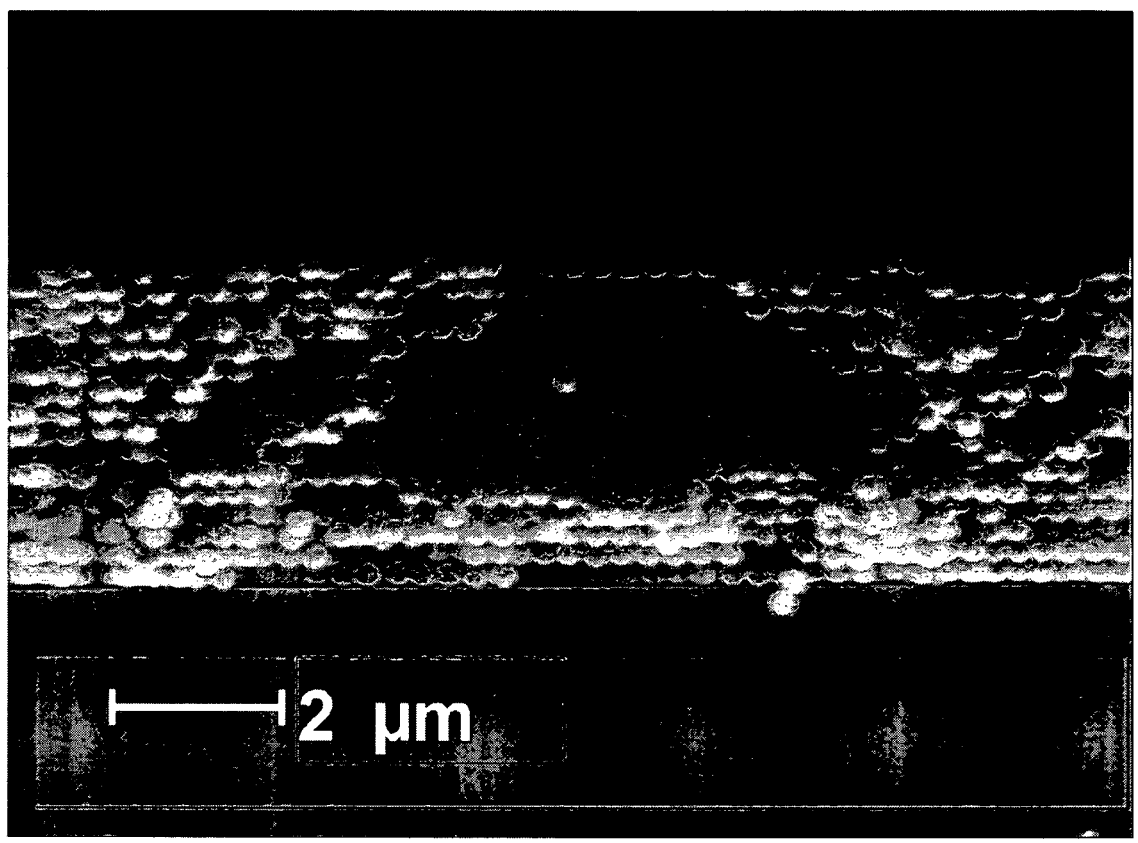
FIG. 4A is a SEM image showing a cross section of a biochip platform manufactured in Example 5.
Figure 4B:
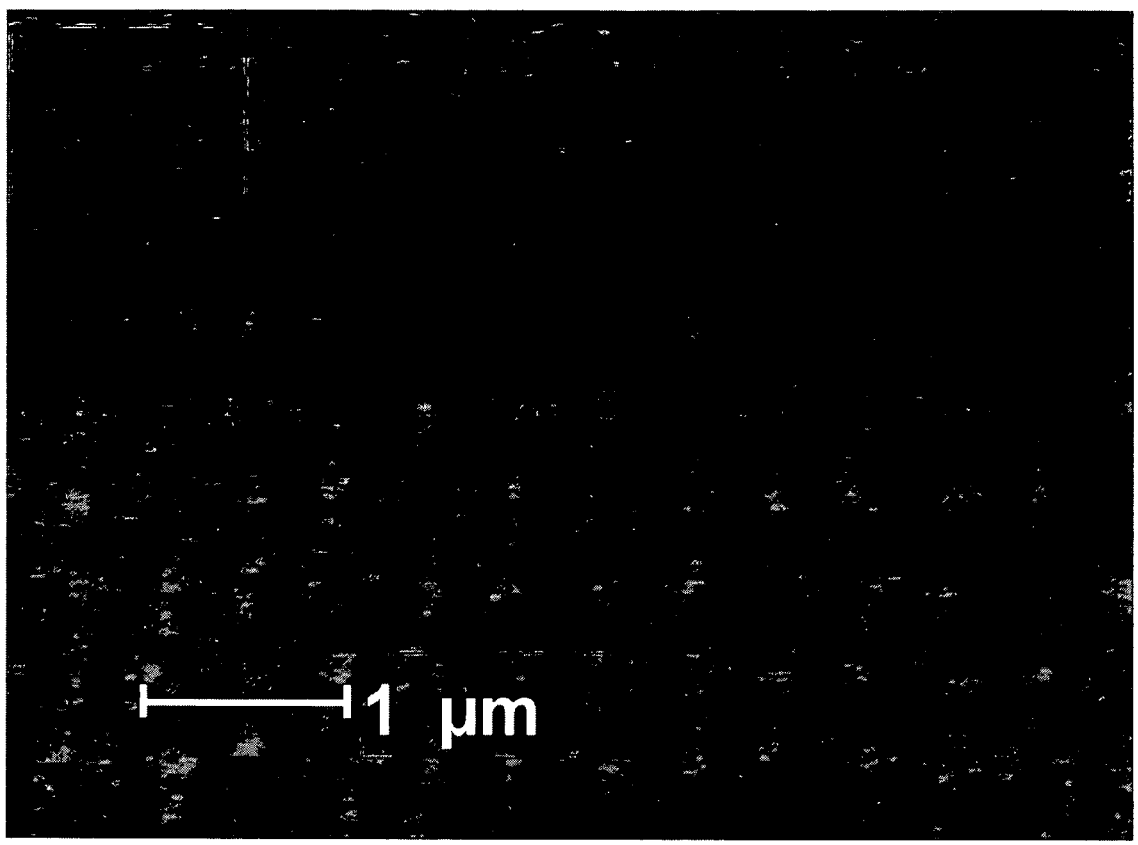
FIG. 4B is a SEM image showing a top surface of the biochip platform manufactured in Example 5.

Silica ($SiO_2$) particles with a particle size of 210 nm were dispersed in isopropyl alcohol to prepare a colloid solution. The colloid solution was applied to a vessel containing a glass substrate with a size of 1 inch×3 inch, and the solvent was evaporated at room temperature for 24 hours to form a silica particle layer having a FCC structure and an average thickness of 5 μm on the glass substrate. To increase a binding force between the silica particles and the glass substrate, the resultant structure was sintered at 600° C. for 4 hours. Surface and sectional images of the silica particle layer are shown in FIGS. 4A and 4B, respectively.

The silica particles were coated with an ethanol solution of aminopropyltriethoxysilane at room temperature for one hour, sufficiently cleaned with ethanol, and incubated at about 110° C. for one hour. The resultant structure was sufficiently cleaned with ethanol and spin-dried. Then, a 80M aminated probe DNA solution, a PEG buffer (in 9.0 mM $NaHCO_3$, pH 10, 0.025 M), and formaldehyde were mixed in a ratio of 1:1:2 to prepare a probe DNA solution. A patch was attached to the resultant structure including the surface-modified silica particle layer, and the probe DNA solution was then injected into the patch. The probe DNAs were allowed to be immobilized on the silica particle layer at room temperature under a predetermined humidity condition for two hours or more. The resultant structure was washed with a 1×SSC buffer for 5 minutes and dried with distilled water. A $Cy_3$-labeled target DNA solution and a 2× hybridization buffer were mixed in a ratio of 1:1 to prepare a target DNA solution. Like in the immobilization with the probe DNAs, hybridization was performed using a patch under a predetermined humidity condition. The resultant structure was washed with a 3×SSC solution for 5 minutes and then a 1×SSC solution for 5 minutes, and dried. The aminated probe DNAs had a sequence of 5'-$NH_2$-CCTCCTCCCCCCTGTCAGCA-3'. When a target concentration was 10 nM, the discrimination ratio between a perfectly matched sequence (3'-GGAG-GAGGGGGGACAGTCGT-5') and a mismatched sequence (3'-CAA GAC AAG AGA ACA-5') in optimal hybridization conditions was 20.

EXAMPLE 6

A biochip platform was manufactured in the same manner as in Example 5 except that silica particles with a particle size of 255 nm were used, and DNA hybridization was performed in the same manner as in Example 5.

EXAMPLE 7

A biochip platform was manufactured in the same manner as in Example 5 except that silica particles with a particle size of 295 nm were used, and DNA hybridization was performed in the same manner as in Example 5.

COMPARATIVE EXAMPLE 1

A fluorescent material (trade name: Alexa Fluor™ 532) was formed as a monolayer on a GAPS-treated glass substrate having a size of 1 inch×3 inch.

COMPARATIVE EXAMPLE 2

GAPS used as a surface-treatment agent was self-assembled on a glass substrate with a size of 1 inch×3 inch, and probe DNAs having a sequence of 5'-NH2-CCTCCTC-CCCCCTGTCAGCA-3' was bound to the surface-treatment agent. Then, Cy3-labeled target DNAs specifically reacting with the probe DNAs were hybridized on the substrate so that the target DNAs were covalently linked to the probe DNAs. The target DNAs had a sequence of Cy3-labeled 3'-GGAG-GAGGGGGGACAGTCGT-5'. Unreacted target DNAs and target DNAs trapped in cavities were removed by washing.

EXPERIMENTAL EXAMPLES

Figure 5:
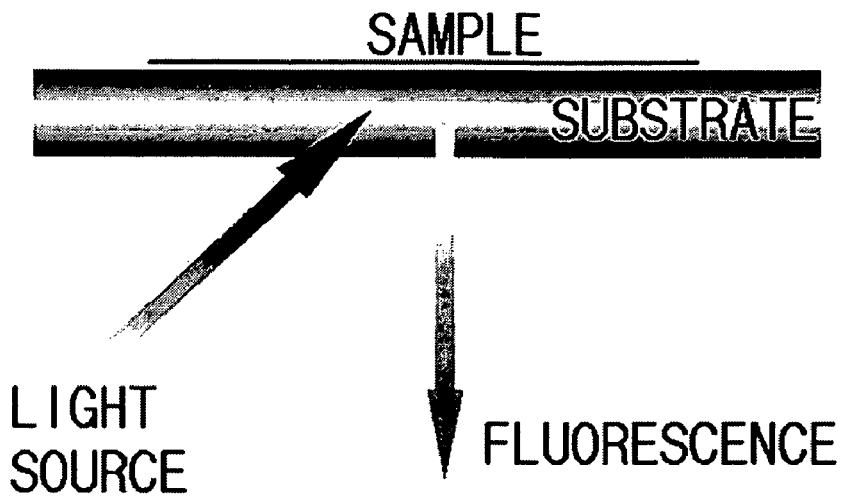
FIG. 5 is a schematic diagram illustrating a conventional fluorescence assay method using a conventional chip platform.

Fluorescence assays for the biochip platforms manufactured in Comparative Example 1 and Examples 3-5 were performed using an optical assay apparatus including a light source and a detector. FIG. 5 illustrates a fluorescence assay method for the biochip platform of Comparative Example 1, FIG. 6A illustrates a fluorescence assay method for the biochip platforms of Examples 3-4, and FIG. 6B illustrates a fluorescence assay method for the biochip platform of Example 5.

Hybridization results in photonic crystals were evaluated using fluoresence intensity, spectrum, and reflectivity at 2D scanning area. 523 nm excitation light was scanned using a confocal fluorescence scanner (Axon Instrument, Genepix 4000B, 5 μm spatial resolution), and the intensity of excitation light-induced Cy3 fluorescence was measured using a bandpass filter (575DF35; Axon Instrument, transmission filter of 550-600 nm, ±10 nm allowance). Fluorescence spectrum with respect to colloidal particle size was measured using a monochromator (Oriel) and a cooled CCD (Oriel). Film thickness measurement was performed using SEM (Hitachi S4700), SpectraThick 2000 (KMAC), and reflectivity was measured using a microscope reflector and a fiber-coupled reflector.

Figure 7:
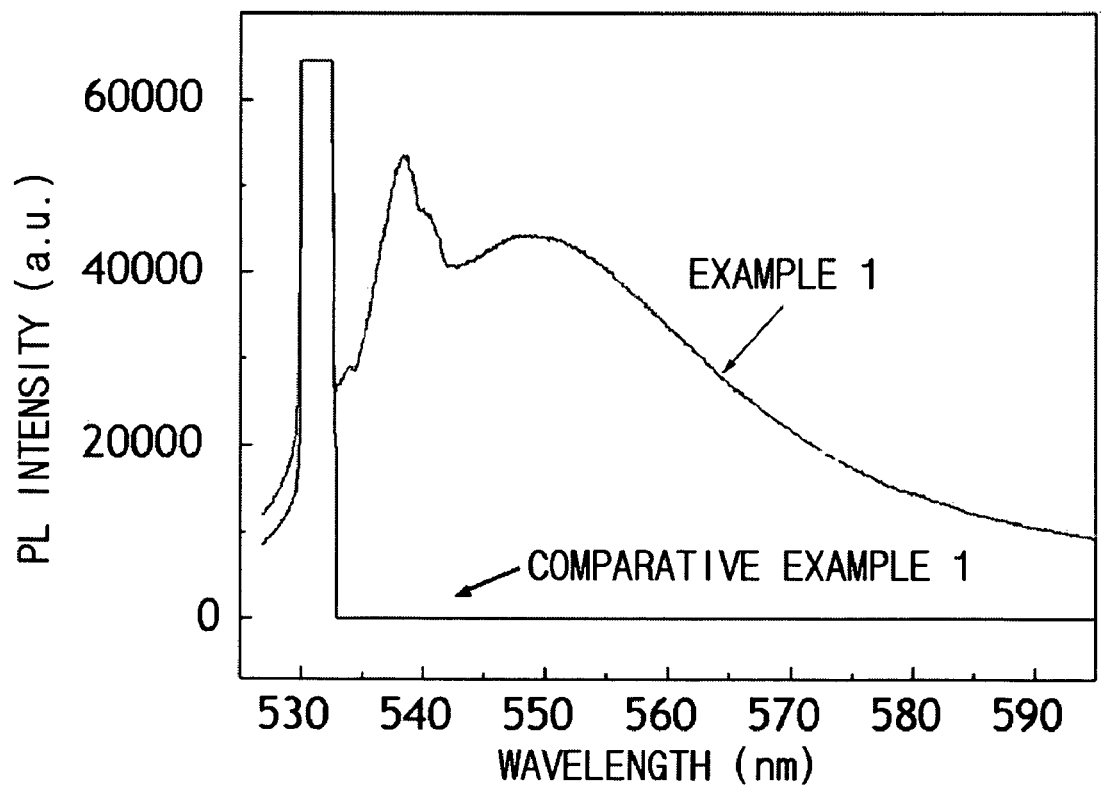
FIG. 7 is a graph illustrating visible PhotoLuminescence (PL) intensities from chip platforms of Example 1 and Comparative Example 1.

Photoluminescene (PL) intensity results analyzed using optical assay apparatuses including the biochip platforms manufactured in Example 1 and Comparative Example 1 are shown in FIG. 7. Referring to FIG. 7, the biochip platform of Example 1 according to the present invention exhibited greatly improved fluorescence signal separation and amplification efficiencies for a target sample, whereas a fluorescence signal was hardly observed in the biochip platform of Comparative Example 1.

Figure 8:
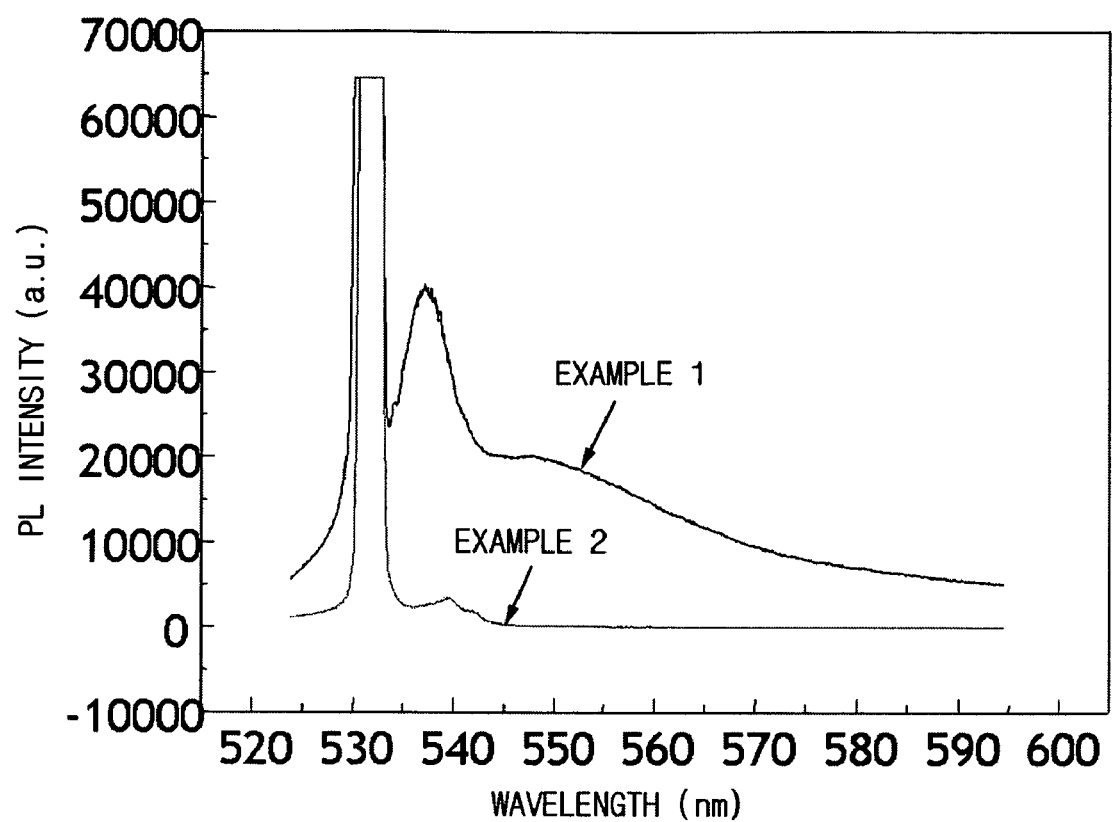
FIG. 8 is a graph illustrating PL intensity with respect to with or without a surface-treatment agent in chip platforms of Examples 1-2.

PL intensity results from the biochip platforms of Examples 1-2 are shown in FIG. 8. Referring to FIG. 8, the biochip platform with the surface-treatment agent of Example 1 showed more excellent PL intensity due to efficient attachment of bioprobes, as compared to the biochip platform with no surface-treatment agent of Example 2.

Figure 9:
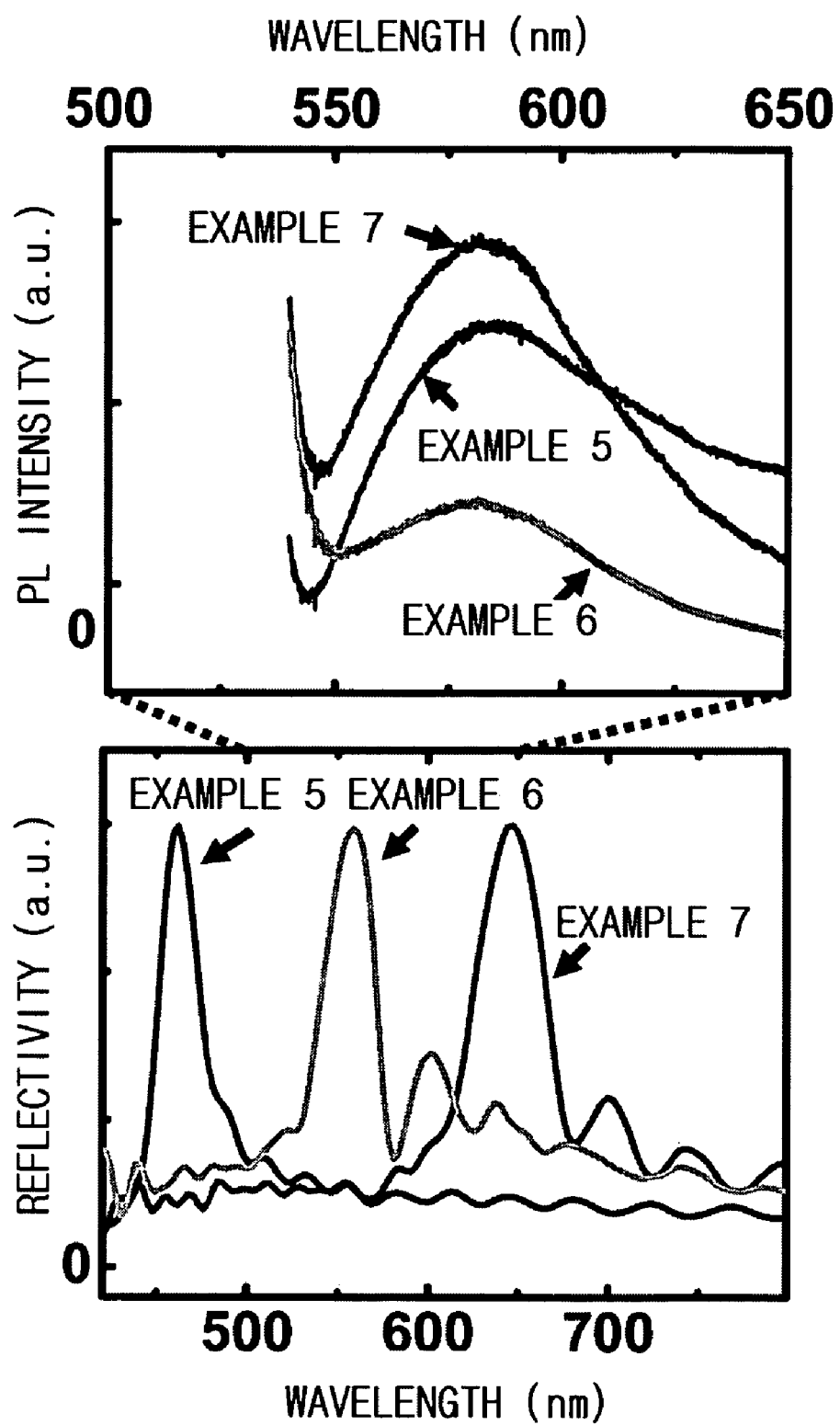
FIG. 9 is a graph illustrating reflection peak positions and fluorescence intensities for biochip platforms of Examples 5-7.

The absorption peak positions for the biochip platforms of Examples 5-7 were analyzed using a reflectometer, and the results are shown in FIG. 9. Referring to FIG. 9, as the size of the silica particles increased (210 nm, 255 nm, and 295 nm), the reflection peak position was shifted to a longer wavelength (about 462 nm, about 560 nm, and about 646 nm).

Figure 10:
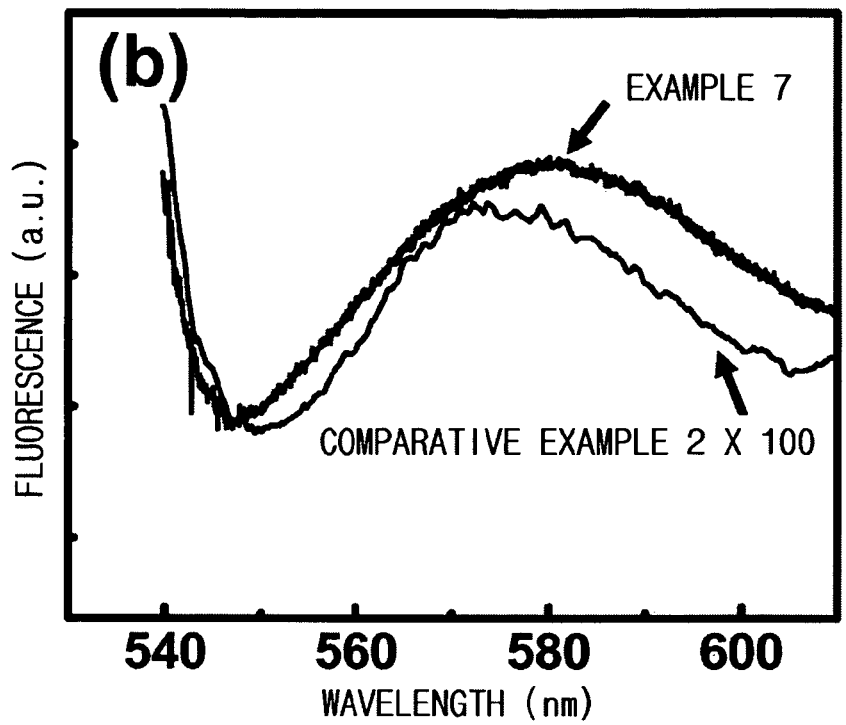
FIG. 10 is a graph illustrating fluorescence intensity with respect to wavelength in biochip platforms of Example 7 and Comparative Example 2.

FIG. 10 illustrates fluorescence intensity from the biochip platforms manufactured in Example 7 and Comparative Example 2 after DNA hybridization. Referring to FIG. 10, the biochip platform including the dielectric particle layer of Example 7 according to the present invention exhibited about 100-fold higher amplification efficiency than the biochip platform with no dielectric particle layer of Comparative Example 2. This result reveals that the large surface area of a dielectric particle layer according to the present invention can significantly enhance a fluorescence signal amplification efficiency.

Figure 11:
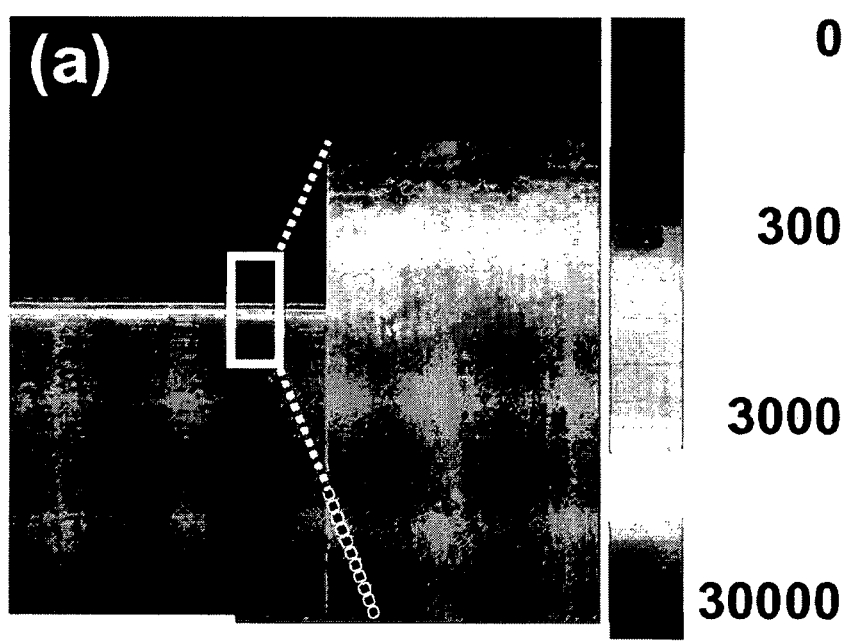
FIG. 11 is a spectrum illustrating fluorescence intensity at an interface between a particle layer and a substrate in the biochip platform of Example 7.

FIG. 11 is a spectrum illustrating fluorescence intensity at an interface between the dielectric particle layer and the substrate in the biochip platform of Example 7. Referring to FIG. 11, as the thickness of the dielectric particle layer increased, fluorescence intensity was increased. Such an increase of fluorescence intensity can be explained as follows. As the thickness of a dielectric particle layer increases, a surface area is increased, and thus, the content of probes attached to the particle layer is increased, thereby increasing fluorescence intensity.

As described above, a biochip platform according to the present invention includes a spherical dielectric particle layer uniformly formed on a substrate. The particle uniformity of the dielectric particle layer enables good wavelength separation of fluorescence signal, and the large surface area of the dielectric particle layer guarantees better amplification efficiency of fluorescence signal. Furthermore, the biochip platform shows good economical efficiency due to easy fabrication process, and is particularly useful in an optical assay apparatus for analyzing a biochemical sample due to good assay efficiency.

What is claimed is:
1. A biochip platform comprising:
a substrate;
a dielectric particle layer formed on the substrate, wherein the dielectric particle layer comprises spherical dielec- tric particles which have been surface modified with a surface-treatment agent; and probes attached to surfaces of dielectric particles constituting the dielectric particle layer via the surface-treatment agent;

wherein the dielectric particle layer has a photonic crystal structure and wherein the photonic crystal structure is a face-centered-cubic (FCC) structure.

2. The biochip platform of claim 1, wherein the energy bandgap of the photonic crystal structure is determined by the particle size of the dielectric particles or refractive index.

3. The biochip platform of claim 1, wherein the probes are oligonucleotides or proteins.

4. An optical assay apparatus comprising:
a light source generating excitation light for exciting a sample;
the biochip platform of claim 3; and
a detector detecting detection light from the sample.

5. The optical assay apparatus of claim 4, wherein the excitation light from the light source is incident into the dielectric particle layer of the biochip platform or a bottom surface of the substrate.

6. The biochip platform of claim 1, wherein the dielectric particles of the dielectric particle layer are made of a dielectric material selected from silica, ZnSe, CdS, polystyrene, polymethylmethacrylate (PMMA), and $Fe_3O_4$.

7. An optical assay apparatus comprising:
a light source generating excitation light for exciting a sample;
the biochip platform of claim 6; and
a detector detecting detection light from the sample.

8. The optical assay apparatus of claim 7, wherein the excitation light from the light source is incident into the dielectric particle layer of the biochip platform or a bottom surface of the substrate.

9. The biochip platform of claim 1, wherein the dielectric particles of the dielectric particle layer have an average particle size of 100 to 1,000 nm.

10. An optical assay apparatus comprising:
a light source generating excitation light for exciting a sample;
the biochip platform of claim 9; and
a detector detecting detection light from the sample.

11. The optical assay apparatus of claim 10, wherein the excitation light from the light source is incident into the dielectric particle layer of the biochip platform or a bottom surface of the substrate.

12. The biochip platform of claim 1, wherein the dielectric particle layer has a thickness of 100 nm to 100 μm.

13. An optical assay apparatus comprising:
a light source generating excitation light for exciting a sample;
the biochip platform of claim 12; and
a detector detecting detection light from the sample.

14. The optical assay apparatus of claim 13, wherein the excitation light from the light source is incident into the dielectric particle layer of the biochip platform or a bottom surface of the substrate.

15. The biochip platform of claim 1, wherein the dielectric particle layer is formed by gravity sedimentation or evaporation.

16. An optical assay apparatus comprising:
a light source generating excitation light for exciting a sample;
the biochip platform of claim 15; and
a detector detecting detection light from the sample.

17. The optical assay apparatus of claim 16, wherein the excitation light from the light source is incident into the dielectric particle layer of the biochip platform or a bottom surface of the substrate.

18. The biochip platform of claim 1, wherein the substrate is a transparent substrate.

19. The biochip platform of claim 18, wherein the transparent substrate is a glass substrate coated with $TiO_2$, $SiN_3$, or indium tin oxide (ITO), or a Si substrate.

20. An optical assay apparatus comprising:
a light source generating excitation light for exciting a sample;
the biochip platform of claim 19; and
a detector detecting detection light from the sample.

21. The optical assay apparatus of claim 20, wherein the excitation light from the light source is incident into the dielectric particle layer of the biochip platform or a bottom surface of the substrate.

22. An optical assay apparatus comprising:
a light source generating excitation light for exciting a sample;
the biochip platform of claim 18; and
a detector detecting detection light from the sample.

23. The optical assay apparatus of claim 22, wherein the excitation light from the light source is incident into the dielectric particle layer of the biochip platform or a bottom surface of the substrate.

24. An optical assay apparatus comprising:
a light source generating excitation light for exciting a sample;
the biochip platform of claim 1; and
a detector detecting detection light from the sample.

25. The optical assay apparatus of claim 24, wherein the excitation light from the light source is incident into the dielectric particle layer of the bio chip platform or a bottom surface of the substrate.

26. The biochip platform of claim 1, wherein the surface-treatment agent comprises silanes, epoxies, carboxyls, amines, or aldehydes.

27. The biochip platform of claim 1, wherein the surface-treatment agent comprises aminopropyltriethoxysilane (APTES), glycidoxypropyltrimethoxysilane (GPTS), triethoxysilane undecanoic acid (TETU), poly(lysine), or 4-trimethoxysilylbenzaldehyde.

28. An optical assay apparatus comprising:
a light source generating excitation light for exciting a sample;
the biochip platform of claim 2; and
a detector detecting detection light from the sample.

29. The optical assay apparatus of claim 28, wherein the excitation light from the light source is incident into the dielectric particle layer of the biochip platform or a bottom surface of the substrate.

* * * * *